United States Patent
Hembrough et al.

(10) Patent No.: US 10,722,531 B2
(45) Date of Patent: Jul. 28, 2020

(54) OPRT EXPRESSION AND CANCER TREATMENT OUTCOME

(71) Applicant: NantOmics, LLC, Culver City, CA (US)

(72) Inventors: Todd A. Hembrough, Gaithersburg, MD (US); Fabiola Cecchi, Potomac, MD (US); Dongyao Yan, Rockville, MD (US)

(73) Assignee: NantOmics, LLC, Culver City, CA (US)

( * ) Notice: Subject to any disclaimer, the term of this patent is extended or adjusted under 35 U.S.C. 154(b) by 0 days.

(21) Appl. No.: 16/273,350

(22) Filed: Feb. 12, 2019

(65) Prior Publication Data
US 2019/0262369 A1 Aug. 29, 2019

Related U.S. Application Data (60) Provisional application No. 62/629,985, filed on Feb. 13, 2018.

(51) Int. Cl.
| | |
|---|---|
| *A61K 31/7072* | (2006.01) |
| *A61K 31/282* | (2006.01) |
| *G01N 33/574* | (2006.01) |
| *A61P 35/00* | (2006.01) |
| *G01N 33/68* | (2006.01) |

(52) U.S. Cl.
CPC ........ *A61K 31/7072* (2013.01); *A61K 31/282* (2013.01); *A61P 35/00* (2018.01); *G01N 33/57419* (2013.01); *G01N 33/6851* (2013.01); *G01N 2496/00* (2013.01); *G01N 2560/00* (2013.01)

(58) Field of Classification Search
CPC ... A61K 31/282; A61K 31/7072; A61P 35/00; G01N 1/44; G01N 2333/91142; G01N 2496/00; G01N 2560/00; G01N 2800/52; G01N 33/57419; G01N 33/6851
See application file for complete search history.

(56) References Cited

U.S. PATENT DOCUMENTS

| | | | |
|---|---|---|---|
| 7,473,532 B2 | 1/2009 | Darfler et al. | |
| 2014/0357512 A1* | 12/2014 | Yang | G01N 33/57407 506/9 |
| 2019/0216795 A1* | 7/2019 | Cecchi | A61K 31/282 |
| 2019/0353660 A1* | 11/2019 | Hembrough | G01N 33/6848 |

OTHER PUBLICATIONS

Ochiai et al. Impact of 5-fluorouracil metabolizing enzymes on chemotherapy in patients with resectable colorectal cancer. Oncology Reports, vol. 32, pp. 887-892. (Year: 2014).*

Teufel et al. Irinotecan plus folinic acid/continuous 5-fluorouracil as simplified bimonthly FOLFIRI regimen for fist-line therapy of metastatic colorectal cancer. BMC Cancer, vol. 3, pp. 1-8. (Year: 2004).*

Kang et al. Capecitabine/cisplatin versus 5-fluorouracil/cisplatin as first-line therapy in patients with advanced gastric cancer: a randomised phase III noninferiority trial. Annals of Oncology, vol. 20. pp. 666-673. (Year: 2009).*

* cited by examiner

*Primary Examiner* — Marcela M Cordero Garcia
(74) *Attorney, Agent, or Firm* — Harness Dickey & Pierce P.L.C.

(57) ABSTRACT

Improved methods for treating cancer are provided herein by determining if a cancer patient, particularly a colon cancer patient or a gastric cancer patient, will clinically respond in a favorable manner to a therapeutic strategy comprising the FOLFOX regimen (fluorouracil, leucovorin, and oxaliplatin) or a combination of capecitabine and cisplatin. Diagnostic methods for measuring the OPRT, TYMP, and/or UCK2 proteins in a tissue sample, such as a tumor sample, from the patient are provided.

25 Claims, 3 Drawing Sheets

Specification includes a Sequence Listing.

OPRT EXPRESSION AND CANCER TREATMENT OUTCOME

CROSS-REFERENCED APPLICATIONS

This application claims the benefit of U.S. Provisional Application No. 62/629,985 filed on 13 Feb. 2018, the entire contents of which are hereby incorporated by reference.

FIELD

Methods are provided for treating cancer patients, for example colon cancer and/or gastric cancer patients, by assaying tumor tissue surgically-removed from patients and identifying those patients most likely to respond to treatment with a standard chemotherapy strategy comprising administration of the FOLFOX regimen and/or the combination therapy of capecitabine and cisplatin. The FOLFOX regimen comprises treating the cancer patient with the combination of chemotherapy drugs 5-fluorouracil, leucovorin, and oxaliplatin.

BACKGROUND

Fluorouracil (5-FU), also known as Adrucil®, is a chemotherapy agent which is in the antimetabolite and pyrimidine analog families of medications that functions by blocking the production of DNA which has the effect of inhibiting cell division thus preventing tumor cells from dividing and growing. 5-FU acts in several ways, but principally as a thymidylate synthase (TS) inhibitor. Interrupting the action of this enzyme blocks synthesis of the pyrimidine thymidine, which is a nucleoside required for DNA replication. Thymidylate synthase methylates deoxyuridine monophosphate (dUMP) to form thymidine monophosphate (dTMP). Administration of 5-FU causes a scarcity in dTMP, so rapidly dividing cancerous cells undergo cell death via due to no thymine. High levels of thymidylate synthase can overcome the effects of 5-FU while high levels of the TYMP protein promotes the activity of 5-FU.

Leucovorin calcium (LV), also known as folinic acid, does not have cancer-fighting properties but is a medication used to decrease the toxic side effects of chemotherapeutic agents. It is most commonly used in combination with 5-fluorouracil to treat colorectal cancer, but it may also be used to treat folate deficiency that results in anemia.

Oxaliplatin, also known as Eloxatin®, is a cancer chemotherapy agent that interferes with DNA replication thus preventing cells from dividing and leading to tumor cell death via apoptosis. Oxaliplatin has been compared with other platinum compounds used for advanced cancers, such as cisplatin and carboplatin. The retention of a bulky DACH ring by activated oxaliplatin is thought to result in the formation of platinum-DNA adducts in tumor cell DNA, which appear to be more effective at blocking DNA replication and are more cytotoxic than adducts formed from cisplatin. The damaged DNA elicits DNA repair mechanisms, which in turn activates apoptosis when repair proves impossible thus killing the tumor cells.

Capecitabine, also known as Xeloda®, is a chemotherapy agent that, once inside the tumor cell, is converted to 5-fluorouracil (5-EU) through which it acts. It belongs to the class of medications known as fluoropyrimidines, which also includes 5-fluorouracil and tegafur. Thus capecitabine, like 5-FU, acts in several ways, but principally as a thymidylate synthase (TS) inhibitor. Interrupting the action of this enzyme blocks synthesis of the pyrimidine thymidine, which is a nucleoside required for DNA replication. Thymidylate synthase methylates deoxyuridine monophosphate (dUMP) to form thymidine monophosphate (dTMP). Administration of capecitabine causes a scarcity in dTMP, so rapidly dividing cancerous cells undergo cell death via due to no thymine. High levels of thymidylate synthase can overcome the effects of capecitabine while high levels of the TYMP protein promotes the activity of capecitabine.

Cisplatin, also known as Platinol®, is a chemotherapy agent that crosslinks DNA in several different ways, interfering with cell division by mitosis. The damaged DNA elicits DNA repair mechanisms, which in turn activate apoptosis when repair proves impossible. Most notable among the changes in DNA induced by cisplatin are the 1,2-intrastrand cross-links with purine bases. These include 1,2-intrastrand d(GpG) adducts which form nearly 90% of the adducts and the less common 1,2-intrastrand d(ApG) adducts. 1,3-intrastrand d(GpXpG) adducts occur but are readily excised by the nucleotide excision repair (NER). Other adducts include inter-strand crosslinks and nonfunctional adducts that have been postulated to contribute to cisplatin's activity. Interaction with cellular proteins, particularly HMG domain proteins, has also been advanced as a mechanism of interfering with mitosis, although this is probably not its primary method of action. Although cisplatin is frequently designated as an alkylating agent, it has no alkyl group and it therefore cannot carry out alkylating reactions. It is correctly classified as alkylating-like.

SUMMARY

The improved methods of cancer treatment described herein identify cancer patients, particularly colon cancer and/or gastric cancer patients, who are most likely to respond to treatment with administration of the FOLFOX regimen and/or the combination capecitabine/cisplatin by determining levels of the OPRT protein directly in a patient tumor tissue sample via SRM/MRM mass spectrometry.

In further embodiments, levels of the TYMP protein and UCK2 protein are also determined directly in the patient tumor tissue sample, in addition to OPRT.

In particular embodiments, the patient tumor tissue sample is a formalin-fixed tissue sample, such as formalin-fixed paraffin embedded (FFPE) tissue.

In yet additional embodiments, the FFPE tissue is protein digested and analyzed by SRM/MRM mass spectrometry.

DETAILED DESCRIPTION

OPRT, also known as orotate phosphoribosyl transferase and orotidine-5-decarboxylase, is a uridine 5'-monophosphate synthase. The OPRT protein is a bifunctional enzyme that catalyzes the final two steps of the de novo pyrimidine biosynthetic pathway. The first reaction is carried out by the N-terminal enzyme orotate phosphoribosyltransferase which converts orotic acid to orotidine-5'-monophosphate. The terminal reaction is carried out by the C-terminal enzyme OMP decarboxylase which converts orotidine-5'-monophosphate to uridine monophosphate.

OPRT is a prognostic predictor of therapeutic outcome in cancer patients and as such can provide information about chemotherapy treatment strategies of cancer. The presence and/or quantitative levels of OPRT protein expression in patient tumor cells procured from patient tumor tissue is determined by quantitating a specified peptide, or peptides, derived from subsequences the full-length OPRT protein using the methodology of SRM/MRM mass spectrometry. Specific quantitative levels of the OPRT protein as detected by SRM/MRM mass spectrometry in cancer cells present within a cancer patient indicates that the patient is either more likely or less likely to respond in a positive manner to a chemotherapy regimen comprising FOLFOX or the combination therapy capecitabine/cisplatin.

Improved methods for treating cancer are provided herein by determining if a cancer patient, particularly a stage III colon cancer patient or a gastric cancer patient, will clinically respond in a favorable manner to a therapeutic strategy comprising the FOLFOX regimen (5-fluorouracil, leucovorin, and oxaliplatin) or a combination of capecitabine and cisplatin. Specifically, diagnostic methods for measuring the OPRT, TYMP, and/or UCK2 proteins in a tumor sample or samples from the patient are provided. The sample can be advantageously formalin-fixed. The amount of the OPRT, TYMP and/or UCK2 proteins in cells derived from formalin fixed paraffin embedded (FFPE) tissue can be determined by using an SRM/MRM assay capable of measuring a specific OPRT peptide fragment, a specific TYMP peptide, a specific UCK2 peptide fragment, and particular characteristics about the peptide fragments, together or substantially at the same time or substantially simultaneously. The peptide fragments derive from the full-length OPRT, TYMP and UCK2 proteins, wherein the sequence for the OPRT peptide fragment is SEQ ID NO:1 (VTDAIVLLDR), the sequence for the TYMP peptide fragment is SEQ ID NO:2 (DGPALSGPQSR) and the sequence for the UCK2 peptide fragment is SEQ ID NO:3 (LFVDTDADTR). Surprisingly it has been found that these peptides can be reliably detected and quantitated substantially at the same time or substantially simultaneously in digests prepared from FFPE samples of tumor tissue.

More specifically, these SRM/MRM assays can measure these peptides directly in complex protein lysate samples prepared from cells procured from patient tissue samples, such as formalin-fixed cancer patient tissue. The most widely and advantageously available form of tissue, and cancer tissue, from cancer patients is formalin-fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long-term storage at room temperature. Thus molecular analytical methods to analyze formalin-fixed cancer tissue will be the most accepted and heavily utilized methods for analysis of cancer patient tissue.

Further, methods of preparing protein samples from formalin-fixed tissue, such as FFPE tissue, are described in U.S. Pat. No. 7,473,532, the contents of which are hereby incorporated by reference in their entirety. The methods described in U.S. Pat. No. 7,473,532 may conveniently be carried out using Liquid Tissue™ reagents and protocol available from Expression Pathology Inc. (Rockville, Md.). For example, a composition comprising the formalin-fixed tumor sample and a reaction buffer can be heated at a temperature from 80° C. to 100° C. for a period of time from 10 minutes to 4 hours. Additionally, the resulting composition can be treated with an effective amount of a proteolytic enzyme selected from the group consisting of trypsin, chymotrypsin, and endoproteinase Lys-C for a period of time from 30 minutes to 24 hours at a temperature from 37° C. to 65° C. In a particular embodiment, the proteolytic enzyme is trypsin.

Results from these SRM/MRM assays can be used to correlate accurate and precise quantitative levels of the OPRT, TYMP and UCK2 proteins within the specific cancer of the patient from whom the tissue was collected and preserved, including gastric cancer tissue. This not only provides diagnostic/prognostic information about the cancer, but also provides improved methods of cancer treatment as part of which a physician or other medical professional may determine appropriate therapy for the patient. In this case, utilizing these assays can provide information about specific levels of OPRT, TYMP and UCK2 protein expression at substantially the same time, or together, or substantially simultaneously in cancer tissue, and whether or not the patient from whom the cancer tissue was obtained will respond in a favorable way to a therapeutic strategy comprising administering the FOLFOX regimen or the combination capecitabine and cisplatin.

Treating cancer patients with the FOLFOX regimen is a common and effective strategy for preventing cancer from growing and thus prolonging the lives of cancer patients, especially gastric cancer patients. One of the agents in this combination therapy is 5-fluorouracil (5-FU) which is in the antimetabolite and pyrimidine analog families of medications. It functions in multiple ways that involve blocking the action of thymidylate synthase and thus stopping the production of DNA as well as blocking the production of RNA and thus causing apoptosis. The OPRT protein is involved in converting capecitabine and 5-dFUR to active 5-FU. Both of these conversions promotes the activity of exogenously administered 5-FU and thus enhances tumor cell killing by 5-FU. As a result, higher levels of the OPRT protein are desirable when treating the cancer patient with the FOLFOX regimen that includes 5-FU or the combination capecitabine and cisplatin. It therefore is useful for a clinician to know quantitative levels of the OPRT protein in a patient's cancer cells so that either the FOLFOX or combination capecitabine and cisplatin chemotherapeutic regimens can or cannot be administered to the patient according to determined levels.

Additionally, the TYMP protein is involved in converting 5-dFUR to active 5-FU as well as converting 5-FU to FUDR. Both of these conversions promotes the activity of exogenously administered 5-FU and thus enhances tumor cell killing by 5-FU. Thus higher levels of the TYMP protein are desirable when treating the cancer patient with the FOLFOX regimen that includes 5-FU. It therefore is useful for a clinician to know quantitative levels of the TYMP protein in a patient's cancer cells so that either the FOLFOX or combination capecitabine and cisplatin chemotherapeutic regimens can or cannot be administered to the patient according to determined levels.

In similar fashion, the UCK2 protein is also involved in converting 5-dFUR to active 5-FU as well as converting 5-FU to FUDR. Both of these conversions promotes the activity of exogenously administered 5-FU and thus enhances tumor cell killing by 5-FU. Thus higher levels of the UCK2 protein are desirable when treating the cancer patient with a regimen that includes 5-FU. It therefore is useful for a clinician to know quantitative levels of the UCK2 protein in a patient's cancer cells so that either the FOLFOX or combination capecitabine and cisplatin chemotherapeutic regimens can or cannot be administered to the patient according to determined levels.

Presently the most widely-used and applied methodology to determine protein presence in cancer patient tissue, especially FFPE tissue, is immunohistochemistry (IHC). IHC methodology utilizes an antibody to detect the protein of interest. The results of an IHC test are most often interpreted by a pathologist or histotechnologist. This interpretation is subjective and does not provide quantitative data that are predictive of sensitivity to therapeutic agents that target specific oncoprotein targets, such as 5-FU and capecitabine sensitivity in an OPRT, TYMP and UCK2 positive tumor cell population.

Research from other IHC assays, such as the Her2 IHC test suggest the results obtained from such tests may be wrong or misleading. This is probably because different labs have different rules for classifying positive and negative IHC status. Each pathologist running the tests also may use different criteria to decide whether the results are positive or negative. In most cases, this happens when the test results are borderline, meaning that the results are neither strongly positive nor strongly negative. In other cases, tissue from one area of cancer tissue can test positive while tissue from a different area of the cancer tests negative. Inaccurate IHC test results may mean that patients diagnosed with cancer do not receive the best possible care. If all or part of a cancer is positive for a specific target oncoprotein but test results classify it as negative, physicians are unlikely to recommend the correct therapeutic treatment, even though the patient could potentially benefit from those agents. If a cancer is oncoprotein target negative but test results classify it as positive, physicians may recommend a specific therapeutic treatment, even though the patient is unlikely to get any benefits and is exposed to the agent's secondary risks.

Thus there is great clinical value in the ability to correctly evaluate quantitative levels of the OPRT, TYMP and UCK2 proteins in tumors, especially colorectal tumors, so that the patient will have the greatest chance of receiving the most optimal treatment.

Detection of peptides and determining quantitative levels of specified OPRT, TYMP and UCK2 fragment peptides can be determined in a mass spectrometer by the SRM/MRM methodology, whereby the SRM/MRM signature chromatographic peak area of each peptide is determined within a complex peptide mixture present in a Liquid Tissue™ lysate (see U.S. Pat. No. 7,473,532, as described above). Quantitative levels of the OPRT, TYMP and UCK2 proteins can then be determined by the SRM/MRM methodology whereby the SRM/MRM signature chromatographic peak area of an individual specified peptide from each of the OPRT, TYMP and UCK2 proteins in one biological sample is compared to the SRM/MRM signature chromatographic peak area of a known amount of a "spiked" internal standard for each of the individual specified OPRT, TYMP and UCK2 fragment peptides. In one embodiment, the internal standard is a synthetic version of the same exact OPRT, TYMP and UCK2 fragment peptides where the synthetic peptides contain one or more amino acid residues labeled with one or more heavy isotopes. Such isotope labeled internal standards are synthesized so that mass spectrometry analysis generates a predictable and consistent SRM/MRM signature chromatographic peak that is different and distinct from the native OPRT, TYMP and UCK2 fragment peptide chromatographic signature peaks and which can be used as comparator peaks. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

To develop the SRM/MRM assay for the OPRT, TYMP and UCK2 fragment peptides additional information beyond simply the peptide sequence needs to be utilized by the mass spectrometer. That additional information is important in directing and instructing the mass spectrometer, (e.g., a triple quadrupole mass spectrometer) to perform the correct and focused analysis of the specified OPRT, TYMP and UCK2 fragment peptides. A triple quadrupole mass spectrometer is suitable instrument for analyzing a single isolated target peptide within a very complex protein lysate that may consist of hundreds of thousands to millions of individual peptides from all the proteins contained within a cell. The additional information provides the triple quadrupole mass spectrometer with the correct directives to allow analysis of a single isolated target peptide within a very complex protein lysate that may consist of hundreds of thousands to millions of individual peptides from all the proteins contained within a cell. Although SRM/MRM assays can be developed and performed on any type of mass spectrometer, including a MALDI, ion trap, ion trap/quadrupole hybrid, or triple quadrupole, presently the most advantageous instrument platform for SRM/MRM assay is often considered to be a triple quadrupole instrument platform. The additional information about target peptides in general, and in particular about the specified OPRT, TYMP and UCK2 fragment peptides, may include one or more of the mono isotopic mass of each peptide, its precursor charge state, the precursor m/z value, the m/z transition ions, and the ion type of each transition ion. The peptide sequence of the specified OPRT, TYMP and UCK2 fragment peptides is shown in Table 1.

TABLE 1

| SEQ ID | Peptide Sequence |
| --- | --- |
| SEQ ID NO: 1 | VTDAIVLLDR |
| SEQ ID NO: 2 | DGPALSGPQSR |
| SEQ ID NO: 3 | LFVDTDADTR |

Because both nucleic acids and protein can be analyzed from the same Liquid Tissue™ biomolecular preparation it is possible to generate additional information about disease diagnosis and drug treatment decisions from the nucleic acids in the same sample upon which proteins were analyzed. For example, if the OPRT, TYMP and UCK2 proteins are expressed by certain cells at increased levels, when assayed by SRM the data can provide information about the state of the cells and their potential for uncontrolled growth, choice of optimal therapy, and potential drug resistance. At the same time, information about the status of genes and/or the nucleic acids and the proteins they encode (e.g., mRNA molecules and their expression levels or splice variations) can be obtained from nucleic acids present in the same Liquid Tissue™ biomolecular preparation. Nucleic acids can be assessed at substantially the same time or substantially simultaneously or together with the SRM analysis of proteins, including the OPRT, TYMP and UCK2 proteins. In one embodiment, information about the OPRT, TYMP and UCK2 proteins and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

In one embodiment, a method of treating cancer in a patient in need thereof, particularly stage III colon cancer, may comprise:
(a) quantifying the level of a OPRT fragment peptide in a protein digest prepared from a tumor tissue sample obtained from a patient and calculating the level of the OPRT peptide in said sample by selected reaction monitoring using mass spectrometry;
(b) treating the patient with a therapeutic regimen comprising administration of the FOLFIRI regimen (irinotecan/5-fluorouracil/folinic acid) when the level of the OPRT fragment peptide is above said reference level, and
(c) treating the patient with a therapeutic regimen other than the regimen comprising administration of the FOLFIRI regimen (irinotecan/5-fluorouracil/folinic acid) when the level of the OPRT fragment peptide is below said reference level.

In another embodiment, a method of treating cancer in a patient in need thereof, particularly a gastric cancer, may comprise
(a) quantifying the level of a OPRT fragment peptide in a protein digest prepared from a tumor tissue sample obtained from a patient and calculating the level of the OPRT peptide in said sample by selected reaction monitoring using mass spectrometry;
(b) treating the patient with a therapeutic regimen comprising administration of the combination of capecitabine and cisplatin when the level of the OPRT fragment peptide is above said reference level, and
(c) treating the patient with a therapeutic regimen other than the regimen combination of capecitabine and cisplatin when the level of the OPRT fragment peptide is below said reference level.

In another embodiment, a method of treating cancer in a subject in need thereof, especially gastric cancer, may comprise:
(a) quantifying the level of a OPRT fragment peptide and quantifying the level of a TYMP fragment and quantifying the level of a UCK2 fragment peptide in a protein digest prepared from a tumor tissue sample obtained from the patient and calculating the levels of the OPRT, TYMP and UCK2 peptides in said sample by selected reaction monitoring using mass spectrometry;
(b) comparing the level of said OPRT, TYMP and UCK2 fragment peptides to reference levels, and
(c) treating the patient with a therapeutic regimen other than the regimen combination of capecitabine and cisplatin when the level of one or more, two, or three of the OPRT, TYMP, and UCK2 fragment peptides are below said reference levels.

In a particular embodiment, the tumor tissue sample is formalin-fixed paraffin embedded (FFPE) tissue which is protein digested, with for example trypsin.

EXAMPLES

To determine an appropriate reference level for OPRT, TYMP and UCK2 quantitation, tumor samples were obtained from a cohort of patients suffering from cancer, in this case gastric cancer and stage III colon cancer. The tumor samples were formalin-fixed using standard methods and the level of OPRT, TYMP and UCK2 in the samples were measured using the methods as described above. The tissue samples may also be examined using IHC and FISH using methods that are well known in the art. The patients in one cohort had stage III colorectal cancer and in the other cohort had gastric cancer. All stage III colon cancer patients were subsequently treated after surgery with the FOLFOX (5-fluorouracil, leucovorin, and oxaliplatin) regimen while all patients with gastric cancer were subsequently treated after surgery with the combination of capecitabine and cisplatin. Patient response was measured using methods that are well known in the art, for example by recording the progression-free survival (PFS) and/or overall survival (OS) of the patients at time intervals after treatment. A suitable reference level was determined using statistical methods that are well known in the art, for example by determining the lowest p value of a log rank test. Once a reference level had been determined it was used to identify those patients whose OPRT, TYMP and UCK2 protein expression levels indicate that they may likely benefit from the combination of the FOLFOX treatment regimen or the treatment regimen using the drug combination capecitabine and cisplatin. The skilled artisan will recognize the FOLFOX regimen comprising 5-fluorouracil+leucovorin+oxaliplatin is a common treatment regimen for colorectal cancer patients. The skilled artisan will recognize the combination of capecitabine and cisplatin is also a common treatment regimen for gastric cancer patients. Levels of OPRT, TYMP and UCK2 proteins in patient tumor samples are typically expressed in amol/μg, although other units can be used. The skilled artisan will recognize that a reference level can be expressed as a range around a central value, for example, +/−250, 150, 100, 50 or 25 amol/μg.

Example 1

Figure 1:
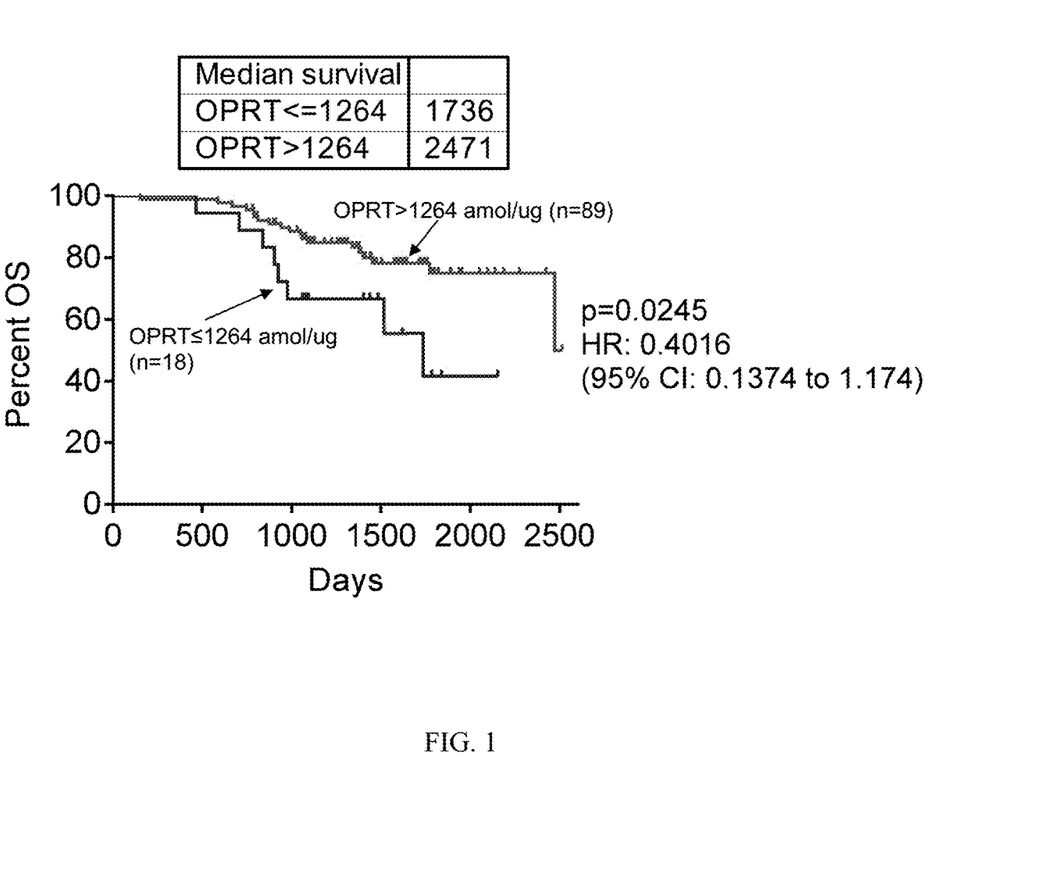
FIG. 1 shows that OPRT was assessed in stage III colon cancer patients by determining the association between its protein levels and Overall Survival (OS) for treatment with the FOLFOX regimen. Kaplan Meier curves indicate that a threshold of 1264 amol/µg leads to significant patient population separation. 89 stage III colon cancer patients show OPRT levels >1264 amol/µg and 18 stage III colon cancer patients show OPRT levels ≤1264 amol/µg. Median stage III colon cancer patient overall survival increased from 1736 days to 2471 days based on this cutoff.

FIG. 1 shows that OPRT was assessed in stage III colon cancer patients by determining the association between its protein levels and Overall Survival (OS) in a univariate Cox model for treatment with the FOLFOX (5-fluorouracil, leucovorin, and oxaliplatin) regimen. Performing data analysis using the continuous OPRT data a cutoff threshold was derived for dichotomizing patients by OPRT levels using Cox proportional modeling. Kaplan Meier curves of the dataset stratified by binary OPRT groups constructed for visualization. A threshold of 1264 amol/μg was selected to test the possibility of patient population separation. As a continuous variable, there is slight separation of the 2 patient populations and a statistically significant association between OPRT levels and OS (p=0.0245; HR 0.4016 (95% CI: 0.1374 to 1.174). 89 stage III colon cancer patients show OPRT levels >1264 amol/μg and 18 stage III colon cancer patients show OPRT levels ≤1264 amol/μg. Median stage III colon cancer patient overall survival increased from 1736 days to 2471 days based on this cutoff.

Example 2

Figure 2:
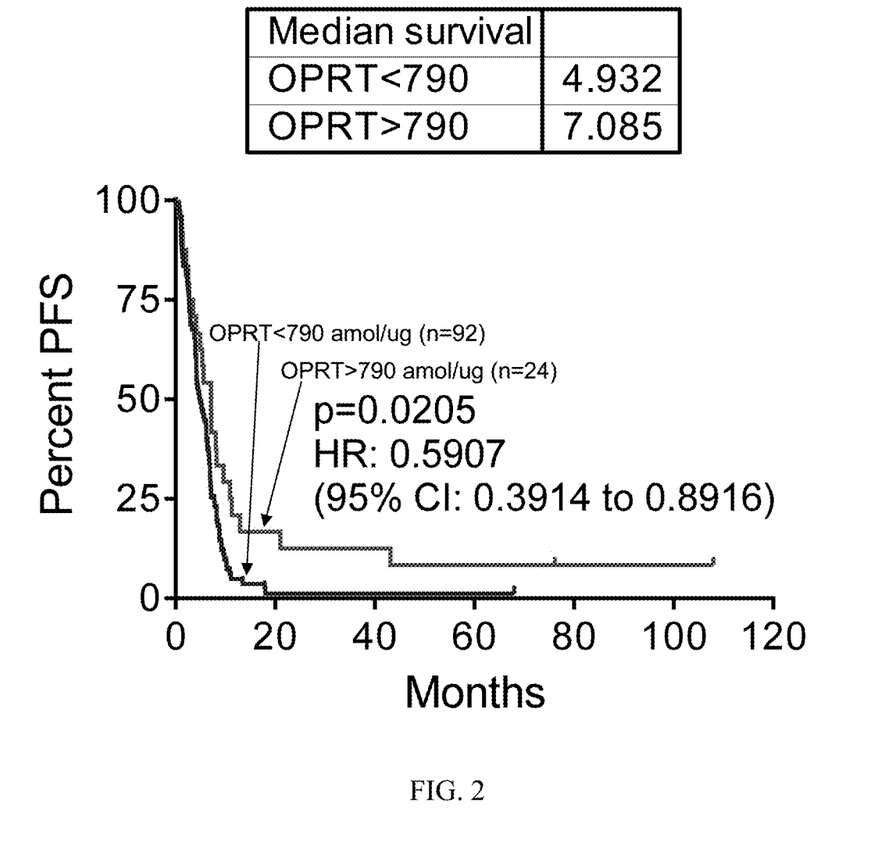
FIG. 2 shows that OPRT was assessed in gastric cancer patients by determining the association between its protein levels and Progression-Free Survival (PFS) for treatment with the chemotherapy combination of capecitabine and cisplatin. Kaplan Meier curves of the dataset indicate a threshold of 790 amol/µg leads to patient population separation that shows a statistically significant association between OPRT levels and PFS. 24 gastric cancer patients show OPRT levels >790 amol/μg and 92 gastric cancer patients show OPRT levels <1264 amol/μg. Median gastric cancer patient progression-free survival increased from 4.923 months to 7.085 months based on this cutoff.

FIG. 2 shows that OPRT was assessed in gastric cancer patients by determining the association between its protein levels and Progression-Free Survival (PFS) in a univariate Cox model for treatment with the chemotherapy combination of capecitabine and cisplatin. Performing data analysis using the continuous OPRT data a cutoff threshold was derived for dichotomizing patients by OPRT levels using Cox proportional modeling. Kaplan Meier curves of the dataset stratified by binary OPRT groups constructed for visualization. A threshold of 790 amol/μg was selected to test the possibility of patient population separation. As a continuous variable, there is separation of the 2 patient populations and a statistically significant association between OPRT levels and PFS (p=0.0205; HR 0.5907 (95% CI: 0.3914 to 0.8916). 24 gastric cancer patients show OPRT levels >790 amol/μg and 92 gastric cancer patients show OPRT levels <1264 amol/μg. Median gastric cancer patient progression-free survival increased from 4.923 months to 7.085 months based on this cutoff.

Example 3

Figure 3A:
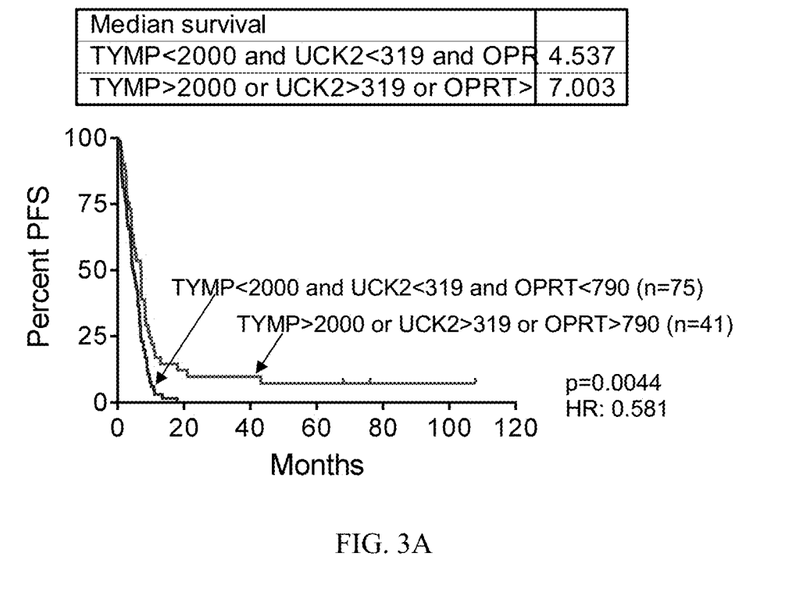
FIG. 3A and FIG. 3B show that OPRT was assessed in gastric cancer patients, in combination with TYMP and UCK2 levels, by determining the association between its protein levels and Progression-Free Survival (PFS) and Overall Survival (OS) for treatment with the chemotherapy combination of capecitabine and cisplatin, respectively. Kaplan Meier curves indicate that the combination of a threshold of 790 amol/μg for OPRT plus a threshold of 2000 amol/μg for TYMP plus a threshold of 319 amol/μg for UCK2 leads to patient population separation that shows a statistically significant association between OPRT, TYMP, and UCK2 levels with PFS and OS. Using these thresholds in combination shows a median gastric cancer patient progression-free survival increased from 4.537 months to 7.003 months based on this cutoff and an increase in overall survival from 8.482 months to 12.66 months.
Figure 3B:
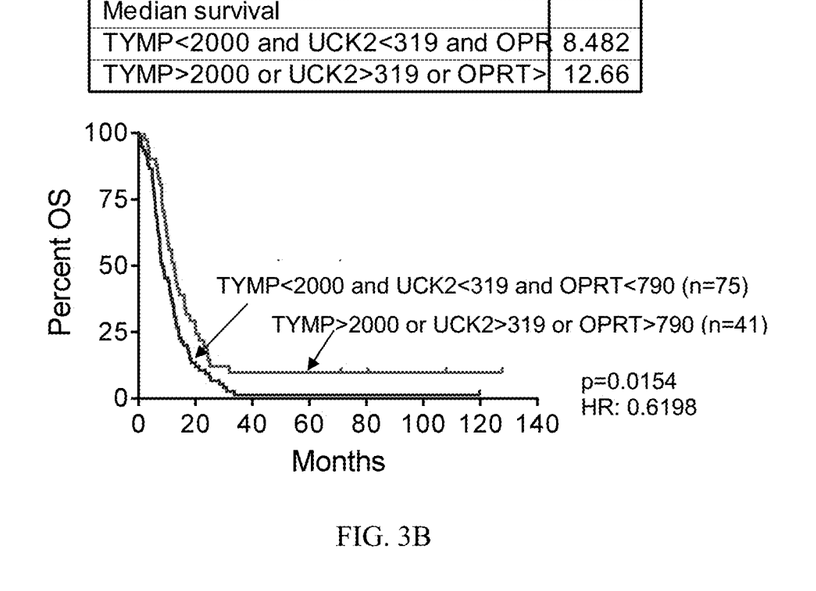

FIG. 3A and FIG. 3B show that OPRT was assessed in gastric cancer patients, in combination with TYMP and UCK2 levels, by determining the association between its protein levels and Progression-Free Survival (PFS) and Overall Survival (OS) for treatment with the chemotherapy combination of capecitabine and cisplatin, respectively. Kaplan Meier curves indicate that the combination of a threshold of 790 amol/μg for OPRT plus a threshold of 2000 amol/μg for TYMP plus a threshold of 319 amol/μg for UCK2 leads to patient population separation that shows a statistically significant association between OPRT, TYMP, and UCK2 levels with PFS and OS. When the thresholds are OPRT >790 amol/μg, TYMP >2000 amol/μg, and UCK2 >319 amol/μg, the PFS is statistically (p=0.0044; HR=0.581) increased from a median PFS of 4.537 months to 7.003 months. When the thresholds are OPRT >790 amol/μg, TYMP >2000 amol/μg, and UCK2 >319 amol/μg, the OS is statistically (p=0.0154; HR=0.6198) increased from a median OS of 8.482 months to 12.66 months.

What is claimed is:

1. A method of treating colon cancer in a patient in need thereof, the method comprising: administering irinotecan, 5-fluorouracil, and folinic acid to the patient,
   wherein a protein digest of a formalin-fixed tissue sample from the patient evidences a level of an OPRT fragment peptide above 1264 amol/μg protein when analyzed by mass spectrometry; and
   wherein the OPRT fragment peptide is a peptide according to SEQ ID NO:1.

2. The method of claim 1, further comprising heating a composition comprising the formalin-fixed tissue sample and a reaction buffer at a temperature from 80° C. to 100° C. for a period of time from 10 minutes to 4 hours.

3. The method of claim 2, further comprising treating the resulting composition with an effective amount of a proteolytic enzyme selected from the group consisting of trypsin, chymotrypsin, and endoproteinase Lys-C for a period of time from 30 minutes to 24 hours at a temperature from 37° C. to 65° C.; and assaying the OPRT fragment peptide level by mass spectrometry.

4. The method of claim 3, wherein the proteolytic enzyme is trypsin.

5. The method of claim 4, wherein the mass spectrometry comprises tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry.

6. The method of claim 5, wherein a mode of the mass spectrometry used is Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

7. The method of claim 1, wherein the formalin-fixed tissue sample is a cell, a collection of cells, or a solid tissue.

8. The method of claim 1, wherein formalin-fixed tissue sample is formalin-fixed paraffin embedded tissue.

9. The method of claim 1, wherein the OPRT fragment peptide level is determined by comparing the amount of the OPRT fragment peptide in the sample to a spiked internal standard peptide of known amount, wherein both the OPRT fragment peptide in the sample and the internal standard peptide correspond to the same amino acid sequence of the OPRT fragment peptide of SEQ ID NO:1.

10. The method of claim 9, wherein the internal standard peptide is an isotopically labeled peptide.

11. The method of claim 10, wherein the isotopically labeled internal standard peptide comprises one or more heavy stable isotopes selected from $^{18}O$, $^{17}O$, $^{15}N$, $^{13}C$, $^{2}H$ and a combination thereof.

12. The method of claim 1, wherein the colon cancer is stage III colon cancer.

13. A method of treating gastric cancer in a patient in need thereof, the method comprising: administering capecitabine and cisplatin to the patient,
   wherein a protein digest of a formalin-fixed tissue sample from the patient evidences a level of an OPRT fragment peptide above 790 amol/μg protein when analyzed by mass spectrometry; and
   wherein the OPRT fragment peptide is a peptide according to SEQ ID NO:1.

14. The method of claim 13, further comprising heating a composition comprising the formalin-fixed tissue sample and a reaction buffer at a temperature from 80° C. to 100° C. for a period of time from 10 minutes to 4 hours.

15. The method of claim 14, further comprising treating the resulting composition with an effective amount of a proteolytic enzyme selected from the group consisting of trypsin, chymotrypsin, and endoproteinase Lys-C for a period of time from 30 minutes to 24 hours at a temperature from 37° C. to 65° C.; and assaying the OPRT fragment peptide level by mass spectrometry.

16. The method of claim 15, wherein the proteolytic enzyme is trypsin.

17. The method of claim 16, wherein the mass spectrometry comprises tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry.

18. The method of claim 17, wherein a mode of the mass spectrometry used is Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

19. The method of claim 13, wherein the formalin-fixed tissue sample is a cell, a collection of cells, or a solid tissue.

20. The method of claim 13, wherein formalin-fixed tissue sample is formalin-fixed paraffin embedded tissue.

21. The method of claim 13, wherein the OPRT fragment peptide level is determined by comparing the amount of the OPRT fragment peptide in the sample to a spiked internal standard peptide of known amount, wherein both the OPRT fragment peptide in the sample and the internal standard peptide corresponds to the same amino acid sequence of the OPRT fragment peptide of SEQ ID NO:1.

22. The method of claim 21, wherein the internal standard peptide is an isotopically labeled peptide comprising one or more heavy stable isotopes selected from $^{18}O$, $^{17}O$, $^{15}N$, $^{13}C$, $^{2}H$ and a combination thereof.

23. The method of claim 13, wherein the protein digest of the formalin-fixed tissue sample from the patient also evidences a level of a TYMP fragment peptide above 2000 amol/μg and a level of a UCK2 fragment peptide above 319 amol/μg protein when assayed by mass spectrometry, and wherein the TYMP fragment peptide is a peptide according to SEQ ID NO:2 and the UCK2 fragment peptide is a peptide according to SEQ ID NO:3.

24. The method of claim 23, wherein
   the TYMP fragment peptide level is determined by comparing the amount of the TYMP fragment peptide in the sample to a spiked internal standard peptide of known amount, wherein both the TYMP fragment peptide in the sample and the internal standard peptide corresponds to the same amino acid sequence of the TYMP fragment peptide of SEQ ID NO:2; and the UCK2 fragment peptide level is determined by comparing the amount of the UCK2 fragment peptide in the sample to a spiked internal standard peptide of known amount, wherein both the UCK2 fragment peptide in the sample and the internal standard peptide corresponds to the same amino acid sequence of the UCK2 fragment peptide of SEQ ID NO:3.

25. The method of claim 24, wherein the internal standard peptide is an isotopically labeled peptide comprising one or more heavy stable isotopes selected from $^{18}O$, $^{17}O$, $^{15}N$, $^{13}C$, $^{2}H$ and a combination thereof.

* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Homo sapiens

<400> SEQUENCE: 1

Val Thr Asp Ala Ile Val Leu Leu Asp Arg
1               5                   10

<210> SEQ ID NO 2
<211> LENGTH: 11
<212> TYPE: PRT
<213> ORGANISM: Homo sapiens

<400> SEQUENCE: 2

Asp Gly Pro Ala Leu Ser Gly Pro Gln Ser Arg
1               5                       10

<210> SEQ ID NO 3
<211> LENGTH: 10
<212> TYPE: PRT
<213> ORGANISM: Homo sapiens
```

```
<400> SEQUENCE: 3

Leu Phe Val Asp Thr Asp Ala Asp Thr Arg
1               5                   10
```